United States Patent [19]

Wehowsky et al.

[11] Patent Number: 4,782,175

[45] Date of Patent: Nov. 1, 1988

[54] URETHANES COMPOSED OF ALIPHATIC FLUOROALCOHOLS, ISOCYANATES AND AROMATIC COMPOUNDS, A PROCESS FOR THEIR PREPARATION AND THEIR USE

[75] Inventors: Frank Wehowsky, Burgkirchen; Rolf Kleber, Neu-Isenburg; Lothar Jaeckel, Flörsheim am Main, all of Fed. Rep. of Germany

[73] Assignee: Hoechst Aktiengesellschaft, Frankfurt am Main, Fed. Rep. of Germany

[21] Appl. No.: 68,924

[22] Filed: Jul. 1, 1987

[30] Foreign Application Priority Data

Jul. 3, 1986 [DE] Fed. Rep. of Germany ....... 3622284

[51] Int. Cl.$^4$ ................. C07C 125/07; C07C 127/04; C07C 147/06
[52] U.S. Cl. ....................................... 560/26; 560/11; 560/13; 560/27; 560/28; 560/29; 560/33; 560/115; 560/133; 560/134; 560/135; 560/137; 260/391; 8/115.51; 8/195
[58] Field of Search ............... 560/26, 115, 158, 11, 560/13, 27, 28, 29, 33, 133, 134, 135, 137

[56] References Cited

U.S. PATENT DOCUMENTS

| 3,657,320 | 4/1972 | Anello | 560/26 |
| 3,681,426 | 8/1972 | Hahn | 560/26 |
| 3,721,700 | 3/1973 | Schuierer | 560/26 |
| 3,746,742 | 7/1973 | Schuierer | 560/26 |
| 4,065,630 | 12/1977 | Sandler | 560/26 |
| 4,289,892 | 9/1981 | Soch | 560/26 |
| 4,321,404 | 3/1982 | Williams | 560/26 |
| 4,525,305 | 6/1985 | Patel | 560/26 |

FOREIGN PATENT DOCUMENTS

| 0172717 | 2/1986 | European Pat. Off. . | |
| 3530967 | 3/1987 | Fed. Rep. of Germany | 560/26 |

Primary Examiner—Michael L. Shippen

[57] ABSTRACT

The molecule of the new urethanes contains an aliphatic fluoroalcohol, an isocyanate and an aromatic dihydroxy, diamino, aminohydroxy, aminocarboxy or hydroxycarboxy compound. They are prepared by reacting an aliphatic fluoroalcohol with a diisocyanate or triisocyanate to give the fluoroalcohol/isocyanate adduct and by reacting this adduct with said aromatic compound to give the desired urethanes composed of an aliphatic fluoroalcohol, an isocyanate and the bifunctional aromatic compound mentioned, and also be reacting a urethane of this type which also carries an active hydrogen atom on the bifunctional aromatic compound, with an isocyanate compound containing one or more isocyanate groups. The new urethanes are preferably used for imparting an oleophobic and hydrophobic finish to textiles and leather.

3 Claims, No Drawings

URETHANES COMPOSED OF ALIPHATIC FLUOROALCOHOLS, ISOCYANATES AND AROMATIC COMPOUNDS, A PROCESS FOR THEIR PREPARATION AND THEIR USE

The invention relates to urethanes composed of aliphatic fluoroalcohols, isocyanates and aromatic compounds. The invention also relates to a process for the preparation of these urethanes and to their use.

It is known from European Patent Application 0,172,717-A2 to improve the textile finishing properties of urethanes composed of at least one aliphatic fluoroalcohol having a perfluoroalkyl group as the fluorine component and a tris-(isocyanatoalkane)-biuret as the isocyanate component, by the incorporation of a modifying group. The modifying group can be an aromatic, aliphatic or alicyclic compound or a mixture of such compounds having one or more active hydrogen atoms (the attachment of the compounds to isocyanate groups is effected via the active hydrogen atoms). Of the modifiers mentioned, essentially only aliphatic compounds are described in detail.

It has now been found, surprisingly, that urethanes containing perfluoroalkyl groups and, if appropriate, epichlorohydrin groups possess particularly good properties in respect of textile finishing if, in addition, they also contain aromatic groups originating from aromatic compounds containing active hydrogen atoms and selected from the group comprising aromatic dihydroxy, diamino, aminohydroxy, aminocarboxy and hydroxycarboxy compounds. The molecule of the new urethane compounds thus contains at least one perfluoroalkyl group and at least one special aromatic compound of the type mentioned, added on by means of an active hydrogen atom, and, if appropriate, at least one epichlorohydrin group.

The urethane compounds according to the invention correspond to the general formula 1 below

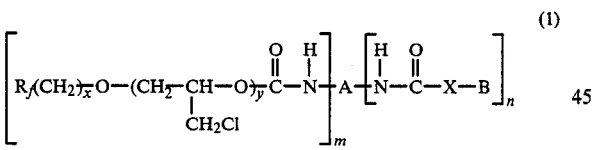

in which:

$R_f$ denotes a perfluoroalkyl group having 4 to 20 carbon atoms, preferably 6 to 16 carbon atoms, or an $R'_fSO_2NR_1$ group in which $R'_f$ has one of the meanings of $R_f$, and $R_1$ is H or an alkyl group having 1 to 4 carbon atoms, x denotes an integer from 1 to 4, preferably 2, y denotes a number from 0 to 10, preferably 1 to 5, m denotes a number from 1 to 2 and n denotes a number from 1 to 2, the sum of m+n being not more than 3, A denotes one of the groups corresponding to the formulae 2 to 10 below (these are isocyanate-free radicals):

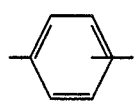
(2)

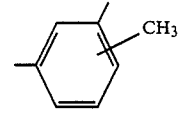
(3)

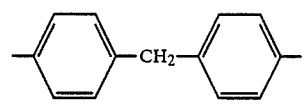
(4)

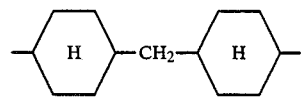
(5)

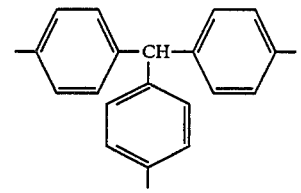
(6)

$+CH_2)_6$ (7)

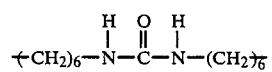
(8)

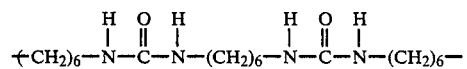
(9)

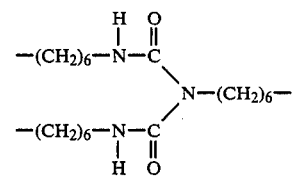
(10)

X denotes one of the groups corresponding to the formulae 11 to 19 below, which can be monosubstituted or polysubstituted, preferably monosubstituted, by an alkyl group having 1 to 4 carbon atoms (the formulae 1 to 19 represent radicals of aromatic dihydroxy, diamino, aminohydroxy, aminocarboxy and hydroxycarboxy compounds which are optionally substituted by $C_1$ to $C_4$ alkyl groups and which, after the release of active hydrogen atoms, are present on isocyanate groups):

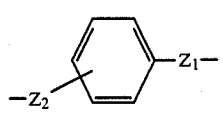
(11)

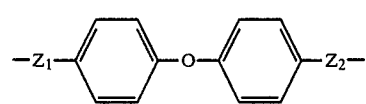
(12)

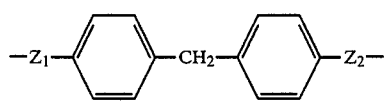
(13)

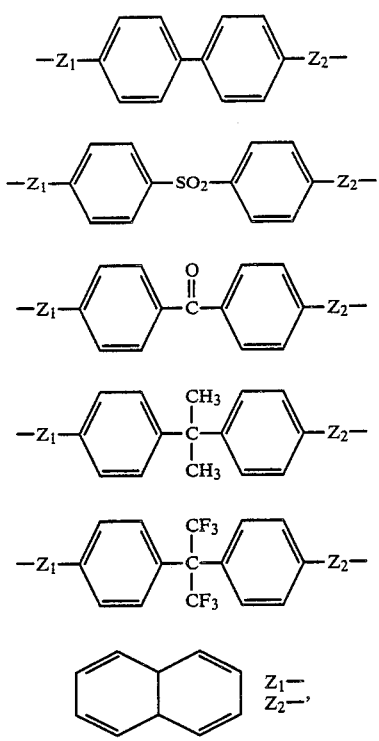

in which $Z_1$ and $Z_2$ represent O, NH or COO in which the two substituents are not identical, or represent O or NH in which the two substituents can also be identical, and B denotes a hydrogen atom, an alkyl group having 1 to 4 carbon atoms or a group corresponding to the formula 20 below

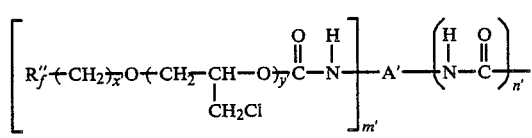

in which $R''_f$, $X'$, $y'$, $m'$, $n'$ and $A'$ have one of the meanings of $R_f$, x, y, m, n and A.

Amongst the meanings indicated for $R_f$, the perfluoroalkyl group having 4 to 20 carbon atoms, preferably 6 to 16 carbon atoms, is preferred. The perfluoroalkyl group can be linear or branched; in the case of a branched perfluoroalkyl group, a terminally branched group is preferred. Of the two perfluoroalkyl groups, the linear or the branched, the linear are preferred. Perfluoroalkyl radicals are, as a rule, a mixture of perfluoroalkyl groups having the abovementioned number of carbon atoms.

A is preferably a toluylene group or one of the three groups corresponding to formulae 8 to 10 (these three groups are, as a rule, present as a mixture). X is preferably a group corresponding to formulae 11, 15, 16, 17 or 18.

B is preferably hydrogen or a group corresponding to formula 20 in which $A'$ is one of the three groups corresponding to formulae 8 to 10.

The preparation of the urethanes according to the invention is evident from the general formula 1 and will be described in greater detail below. These urethanes are prepared by reacting an aliphatic fluoroalcohol of the formula

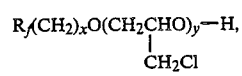

in which $R_f$, x and y have the abovementioned meaning, with a diisocyanate or triisocyanate corresponding to one of the groups of the formulae 2 to 10 to give the adduct of the formula

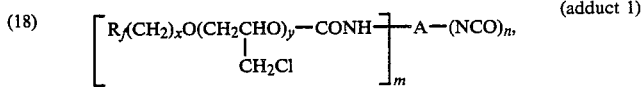

(adduct 1)

in which $R_f$, x, y, m, n and A have the abovementioned meaning, and by reacting the adduct 1 with an aromatic dihydroxy, diamino, aminohydroxy, aminocarboxy or hydroxycarboxy compound of the following formulae

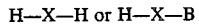

in which X is one of the groups of the formulae 11 to 19 and B is an alkyl group having 1 to 4 carbon atoms, to give the urethanes, according to the invention, of the two formulae 21 and 22 below

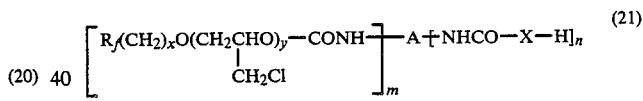

in which $R_f$, x, y, m, n and A have the abovementioned meaning and B is the alkyl group mentioned having 1 to 4 carbon atoms, and by reacting a urethane of the formula 21 with an isocyanate compound containing one or more free isocyanate groups and corresponding to the group of the formula 20, to give the desired urethanes, according to the invention, of the formula 23 below

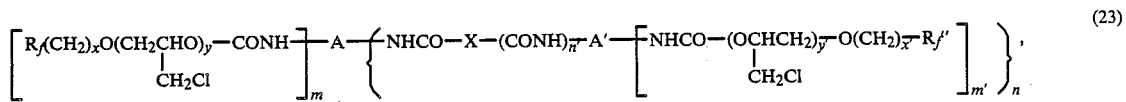

in which $R_f$, $R_f''$, x, x', y, y', m, m', n, n', A, A' and X have the abovementioned meaning.

The preparation of the compounds according to the invention is described in detail below. The adduct 1 is prepared by employing aliphatic fluoroalcohols having one perfluoroalkyl group in the form of a perfluorohydroalkanol or perfluorosulfonamidoalkanol and, if appropriate, having at least one epichlorohydrin group (corresponding to the meaning of Y in formula 1). Perfluorohydroalkanols and perfluorosulfonamidoalkanols such as are employed for the preparation of the adduct 1, if Y is nought in formula 1, have already been known for a long time and therefore no longer need to be described in detail. The aliphatic fluoroalcohols having one perfluoroalkyl group and having epichlorohydrin groups are obtained by reacting, for example, a perfluoroalkylethanol (as the perfluorohydroalkanol) or, for example, a perfluoroalkylsulfonamidoethanol (as the perfluorosulfonamidoalkanol) with epichlorohydrin (boiling point under normal conditions 116° C.) if appropriate in the presence of Lewis acids as a catalyst, at a temperature of 30° to 100° C., preferably 40° to 70° C., the ethanol compound and the epichlorohydrin being employed in a molar ratio of about 1:y (y has the appropriate meaning). The perfluoroalkyl radicals in the perfluorohydroalkanol and in the perfluorosulfonamidoalkanol are, as a rule, low-cost, commercially available mixtures containing essentially 6 to 20 carbon atoms. The nature of the Lewis acid is not critical. Preferred Lewis acids are $BF_3$, boron trifluoride diethyl etherate, $SnCl_4$, $SbCl_5$, 1 $TiCl_4$, $FeCl_3$, $PF_5$ and/or dibutyltin dilaurate, boron trifluoride diethyl etherate being particularly preferred. The amount of catalyst is generally 0.01 to 5% by weight, preferably 0.1 to 1% by weight, relative to the perfluoroalkylethanol. The reaction is preferably carried out with stirring and under the autogenous pressure. The duration of the reaction is within the range from about 0.5 to 7 hours. It can be appropriate to employ a solvent. Preferred solvents are halogenated hydrocarbons, such as carbon tetrachloride, trichloroethylene, 1,2-dichloroethane, trichloroethane and trifluorotrichloroethane; ketones, such as methyl ethyl ketone and cyclohexanone; and ethers, such as diisopropyl ether and tetrahydrofuran. The reaction in question takes place quantitatively. The solvent which may have been used in the resulting reaction product is removed by distillation, in the course of which volatile constituents which may be present, such as unreacted epichlorohydrin, are also removed. The distillation can also, for reasons of suitability, be carried out under a vacuum (water pump vacuum). The Lewis acid employed as a catalyst, which does not in itself interfere in the subsequent reaction with isocyanate can be washed out or neutralized by means of alkaline agents, preferably by means of aqueous sodium bicarbonate solution or an amine, such as triethylamine. The aliphatic fluoroalcohol containing one perfluoroalkyl group and containing epichlorohydrin groups is a wax-like product of a yellow color.

The procedure followed to prepare the adduct 1 is preferably to react an aliphatic fluoroalcohol containing one perfluoroalkyl group and, if appropriate, containing at least one epichlorohydrin group (depending on the meaning of Y in formula 1) with an isocyanate corresponding to the formulae 2 to 10, at a temperature of 70° to 150° C., preferably 90° to 130° C., the aliphatic fluoroalcohol and the isocyanate being employed in the molar ratio arising from the desired meaning of m and n in the formula of the adduct 1. The reaction is preferably carried out with stirring and under the autogenous pressure and—if it is appropriate, for example in order to shorten the reaction time—in the presence of the abovementioned Lewis acid catalysts. It is also possible to employ solvents, for example esters. The reaction time is within the range from 1 to 15 hours. The isocyanates are often commercially available mixtures of isocyanates. Thus the toluylene diisocyanate is composed, as a rule, of about 80% by weight of 2,4-toluylenediisocyanate and 20% by weight of 2,6-toluylenediisocyanate. The isocyanates corresponding to the groups in the formulae 8 to 10 are also, as a rule, present in the form of mixtures. A commercially available and preferred mixture of this type is composed of the three isocyanates in question, the isocyanate corresponding to the formula 10 being present in an amount of at least 50% by weight, relative to the mixture (the isocyanate of the formula 10 is thus the main component in this mixture). The reaction of the aliphatic fluoroalcohol in question with isocyanate to give the adduct 1 takes place quantitatively. The products obtained can, if appropriate, be purified, for example volatile constituents can be removed by distillation. Adduct 1 is a wax-like product of a yellow color.

The procedure followed for the preparation of the compounds, according to the invention, of the formulae 21 and 22 is preferably to react the adduct 1 with an aromatic compound of the formulae H—X—H or H—X—B indicated above, containing active hydrogen atoms, at a temperature of 70° to 150° C., preferably 90° to 130° C., the adduct 1 compound and the aromatic compound carrying active hydrogen atoms being employed in a molar ratio such that the molar amount of aromatic compound corresponds to the free isocyanate groups present in the adduct 1 employed. The reaction is preferably carried out with stirring and under the autogenous pressure and—if it is appropriate, for example in order to shorten the reaction time—in the presence of the abovementioned Lewis acid catalysts. It is also possible to employ solvents, for example esters. The reaction time is within the range from 1 to 40 hours. The reaction of the adduct 1 with the aromatic compound carrying active hydrogen atoms to give the compounds, according to the invention, of the formulae 21 and 22 takes place quantitatively. The product obtained can, if appropriate, be purified, for example volatile constituents can be removed by distillation. The compounds, according to the invention, of the formulae 21 and 22 are wax-like products of a yellow to brown color.

The procedure followed for the preparation of the compounds, according to the invention, of formula 23 is preferably to react a compound of the formula 21 with an isocyanate compound corresponding to the group defined in formula 20 (compare adduct 1) at a temperature of 70° to 150° C., preferably 90° to 130° C., the compound of the formula 21 and the isocyanate compound being employed in a molar ratio such that the molar amount of isocyanate compound corresponds to the active hydrogen atoms present in the compound of the formula 21 employed. Moreover, what has been said above concerning the preparation of the compounds, according to the invention, of the formulae 21 and 22 also applies to the preparation of these compounds according to the invention. Like those of the formulae 21 and 22, the compounds, according to the invention, of the formula 23 are also wax-like products of a yellow to brown color.

The compounds according to the invention are surprisingly good textile treatment agents. They impart to the textiles, above all, an excellent hydrophobic and oleophobic character. They also display to a high extent the property of withstanding, without any loss in effect, the severe stresses to which the finished textiles are exposed, for example when they are stretched, texturized and, in particular, when they are dyed and washed. An unexpected and particularly great advantage of the compounds according to the invention lies in the fact that they can also be employed in customary textile treatment preparations, for example in spinning preparations, and do not thereby lose their excellent action.

The textile material can have a natural and/or synthetic nature. It is preferably composed of polyamide, polyester and/or polyacrylonitrile, polyamide being particularly preferred. The textile material can be in any desired form, for example in the form of filaments, fibers, yarn, flocks, woven fabrics, weft-knitted fabrics, warp-knitted fabrics, carpeting or nonwovens. The amount of compound according to the invention applied is so chosen that 0.02 to 1% by weight of fluorine, preferably 0.04 to 0.4% by weight, of fluorine, calculated from the amount of fluorine in the compound according to the invention, is present on the textile material; percentages by weight relate to the treated textile material. As a rule, the treatment of the textile material with the urethanes according to the invention is carried out either via the textile treatment dressings mentioned above, into which the urethanes according to the invention have been incorporated, or by means of solutions, emulsions or dispersions which have been specially prepared from the urethanes. As a rule they are present in the solutions, emulsions or dispersions and in the textile treatment dressings in a concentration of 5 to 40% by weight and 0.5 to 5% by weight, respectively, preferably 8 to 30% by weight and 1 to 3% by weight, respectively. The treatment of the textiles with the solutions, emulsions or dispersions mentioned is carried out by customary methods, for example by spraying, dipping, padding and the like. The impregnated textile material is then dried and subjected to a heat treatment. As a rule the heat treatment is carried out by heating the textile material to a temperature of 130° to 200° C. and keeping it at this temperature for 10 seconds to 10 minutes. The textile material which has been finished with the urethanes according to the invention possesses the excellent properties mentioned above.

The compounds according to the invention are also excellently suitable for imparting a hydrophobic and oleophobic finish to leather. Examples of leather which may be mentioned are cowhide, goatskin, sheepskin and pigskin leather. The amount of compound according to the invention applied is so chosen that 0.05 to 1.5% by weight of fluorine, preferably 0.1 to 1% by weight of fluorine, calculated on the amount of fluorine in the compound, is present on the leather; percentages by weight relate to the treated leather. The customary procedures for finishing leather can be employed for application.

The invention will now be illustrated in greater detail by means of examples.

COMPOUNDS ACCORDING TO THE INVENTION

EXAMPLE 1

8 kg (15.7 mol) of a commercially available perfluoroalkylethanol mixture in which perfluoroalkyl=$C_8F_{17}$-$C_{16}F_{33}$ (OH number=106), 8 kg of 1,2,2-trifluorotrichloroethane ($CFCl_2$-$CF_2Cl$; boiling point 48° C.) as solvent and 50 g of borontrifluoridediethyletherate as catalyst (i.e. 0.6% by weight of catalyst, relative to perfluoroalkylethanol) were initially placed in a glass flask equipped with a stirrer, a reflux condenser, a thermometer, a dropping funnel and a heating bath. 2.9 kg (31.4 mole) of epichlorohydrin were added dropwise to this solution at 45° C., the mixture being kept at the boiling point of the solvent for 3 hours. The solvent employed was then removed by vacuum distillation (water pump vacuum). The residue was a wax-like product of a yellow color. The molar ratio of perfluoroalkylethanol to epichlorohydrin in the aliphatic fluoroalcohol thus obtained is 1:2 (y in formula 1 has the value 2, resulting from taking an average of 1 to 8 epichlorohydrin units added on). The reaction of the aliphatic fluoroalcohol with isocyanate to give the fluoroalcohol/isocyanate adduct (adduct 1) was carried out in a glass flask equipped with a stirrer, a reflux condenser fitted with a drying tube, a thermometer and a heating bath. 85.0 g (0.13 equivalents) of the aliphatic fluoroalcohol and 35.7 g (0.19 equivalents) of triisocyanate corresponding to formula 10, specifically a commercially available mixture of the three isocyanates corresponding to the formulae 8, 9 and 10, with the triisocyanate as the major constituent, were initially taken (i.e. a molar ratio of 2:1) and were kept at 110° C. for 4 hours, with stirring. 5 drops of dibutyltin dilaurate were then added to the mixture, after which it was kept at 110° C. for 3 hours, with stirring, in order to complete the reaction. The resulting fluoroalcohol/isocyanate adduct (adduct 1) was a wax-like product of a yellow color.

The reaction of the adduct 1 with the aromatic bifunctional compound was also carried out in a glass flask equipped with a stirrer, a reflux condenser fitted with a drying tube, a thermometer and a heating bath. 100.0 g (62.6 milliequivalents) of the adduct 1 and 3.5 g (62.8 milliequivalents) of pyrocatecol were initially taken (i.e. a molar ratio of 2:1) and were kept at 110° C. for 35 hours, with stirring. 100.6 g, i.e. 97.3% by weight of theory, of compound according to the invention were obtained in the form of a wax-like product of a brown color. The overall composition of the compound according to the invention in which the molecule contains an aliphatic fluoroalcohol, isocyanate and pyrocatecol (molar ratio 4:2 1) corresponds to the formula B1 indicated in the table following the examples.

EXAMPLES 2 AND 3

The procedure was as in Example 1, with the exception that resorcinol (Example 2) and hydroquinone (Example 3) were employed instead of pyrocatecol, and that the mixtures were kept at 110° C. for 10 hours in each case, instead of 35 hours. In each case, 102.0 g, i.e. 99.0% by weight of theory, of compound according to the invention were obtained in the form of a wax-like product of a brown color. The overall composition of the two compounds according to the invention in which the molecule contains an aliphatic fluoroalcohol, isocyanate and resorcinol or hydroquinone (molar ratio in each case 4:2:1) correspond to the formulae B2 and B3 indicated in the table mentioned.

EXAMPLE 4

231.4 g (0.12 equivalents) of the adduct 1 from Example 1 and 14.2 g (0.12 equivalents) of 2,2-(4,4'-dihydroxydiphenyl)-propane, i.e. bisphenol A, (i.e. a molar ratio of 2:1) and 62.0 g of di-n-butyl adipate as solvent were initially put into the glass flask indicated above and were kept at 110° C. for 12 hours, with stirring. 5 drops of dibutyltin dilaurate were then added to the mixture, after which it was kept at 110° C. for 4 hours, with stirring, in order to complete the reaction. 304.0 g, i.e. 99.0% by weight of theory, of compound according to the invention were obtained in the form of a wax-like product of a brown color. The overall composition of the compound according to the invention in which the molecule contains an aliphatic fluoroalcohol, isocyanate and bisphenol A (molar ratio 4:2 1) corresponds to the formula B4 indicated in the table mentioned.

EXAMPLE 5

Charge:
154.3 g (80 milliequivalents) of the adduct 1 from Example 1,
13.4 g (80 milliequivalents) of 2,2,-(4,4'-dihydroxydiphenyl)-hexafluoropropane (hexafluorobisphenol A) and
42.0 g of di-n-butyl adipate.
Procedure as in Example 4.

Yield: 205.8 g, i.e. 98.1% by weight of theory, of compound according to the invention in the form of a wax-like product of a brown color. The overall composition of the compound according to the invention in which the molecule contains an aliphatic fluoroalcohol, isocyanate and hexafluorobisphenol A (molar ratio 4:2:1) corresponds to the formula B5.

EXAMPLE 6

Charge:
238.5 g (124.0 milliequivalents) of the adduct 1 from Ex
Example 1,
15.3 g (124.0 milliequivalents) of bis-(4-hydroxyphenyl) sulfone and
64.0 g of di-n-butyl adipate.
Procedure as in Example 4.

Yield: 314.0 g, i.e. 98.5% by weight of theory, of compound according to the invention in the form of a wax-like product of a brown color. The overall composition of the compound according to the invention in which the molecule contains an aliphatic fluoroalcohol, isocyanate and bis-(4-hydroxyphenyl) sulfone (molar ratio 4:2: 1) corresponds to the formula B6.

EXAMPLE 7

Charge:
100.0 g (63.0 milliequivalents) of the adduct 1 from Example 1 and
3.4 g (63.0 milliequivalents) of 3-aminophenol.
Procedure as in Example 1, with the exception that the mixture was kept at 110° C. for 6 hours instead of 35 hours.

Yield: 102.0 g, i.e. 98.7% by weight of theory, of compound according to the invention, in the form of a wax-like product of a brown color. The overall composition of the compound according to the invention in which the molecule contains an aliphatic fluoroalcohol, isocyanate and 3-aminophenol (molar ratio 4:2:1) corresponds to formula B7.

EXAMPLE 8

A further adduct 1 was prepared by initially placing, in the glass flask indicated in Example 1, 162.0 g (0.32 equivalent) of the perfluoroalkylethanol from Example 1, 216.0 g (0.32 equivalent) of the aliphatic fluoroalcohol from Example 1 and 181.3 g (0.96 equivalent) of the triisocyanate from Example 1 (i.e. a molar ratio of 1:1:1) and keeping the mixture at 110° C. for 5 hours, with stirring. The resulting fluoroalcohol/isocyanate adduct (adduct 1) was a wax-like product of a yellow color.

This adduct was reacted with an aromatic bifunctional compound by initially taking, analogously to Example 1, 559.0 g (0.32 equivalent) of the adduct 1, 17.5 g (0.32 equivalent) of hydroquinone and 144.0 g of di-n-butyl adipate as solvent (i.e. a molar ratio of 2:1), and keeping the mixture at 110° C. for 10 hours, with stirring. 715.0 g, i.e. 99.2% by weight of theory, of compound according to the invention were obtained in the form of a wax-like product of a brown color. The overall composition of the compound according to the invention in which the molecule contains an aliphatic fluoroalcohol, isocyanate and hydroquinone (molar ratio 4:2:1) corresponds to the formula B8.

EXAMPLE 9

Charge:
289.3 g (0.15 equivalent) of the adduct 1 from Example 1 and
37.5 g (0.3 equivalent) of bisphenol A.

Procedure as in Example 1, with the exception that the mixture was kept at 110° C. for 7 hours instead of 35 hours and that, after 5 drops of dibutyltin dilaurate had been added, the mixture was kept at 110° C. for a further 6 hours, with stirring, in order to complete the reaction.

Yield: 318.0 g, i.e. 97.5% by weight of theory, of compound according to the invention in the form of a wax-like product of a brown color. The overall composition of the compound according to the invention in which the molecule contains an aliphatic fluoroalcohol, isocyanate and bisphenol A (molar ratio 2:1:1) corresponds to the formula B9.

EXAMPLE 10

Charge:
289.3 g (0.15 equivalent) of the adduct 1 from Example 1 and
37.5 g (0.3 equivalent) of bis-(4-hydroxyphenyl) sulfone.

Procedure as in Example 9. Yield: 323.4 g, i.e. 99.0% of theory, of compound according to the invention in the form of a wax-like product of a brown color. The overall composition of the compound according to the invention in which the molecule contains an aliphatic fluoroalcohol, isocyanate and bis-(4-hydroxyphenyl) sulfone (molar ratio 2:1:1) corresponds to the formula B10.

EXAMPLE 11

Charge:
529.0 g (0.3 equivalent) of the adduct 1 from Example 8 and
33.0 g (0.6 equivalent) of hydroquinone.
Procedure as in Example 8.

Yield: 553.0 g, i.e. 98.5% by weight of theory, of product according to the invention in the form of a wax-like product of a brown color. The overall composition of the compound according to the invention in which the molecule contains an aliphatic fluoroalcohol, isocyanate and hydroquinone (molar ratio 2:1:1) corresponds to the formula B11.

EXAMPLE 12

Charge:

289.3 g (0.15 equivalent) of the adduct 1 from Example 1 and
20.7 g (0.15 equivalent) of para-hydroxybenzoic acid. Procedure as in Example 9.

Yield: 297.0 g, i.e. 95.8% by weight of theory, of compound according to the invention in the form of a wax-like product of a brown color. The overall composition of the compound according to the invention in which the molecule contains an aliphatic fluoroalcohol, isocyanate and parahydroxybenzoic acid (molar ratio 2:1:1) corresponds to the formula B12.

TABLE

No. Chemical formulae of the compounds according to the invention from Examples 1 to 12

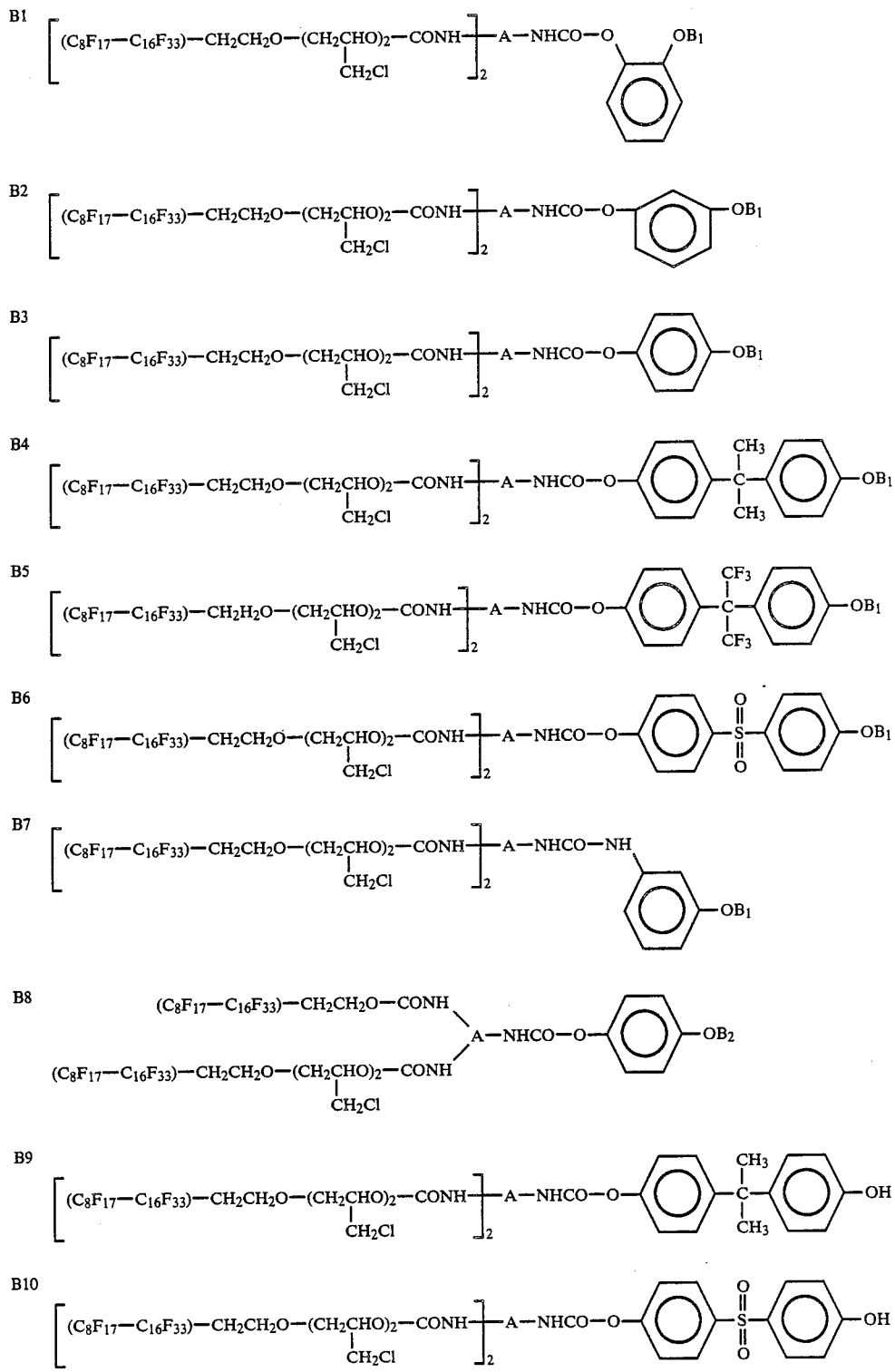

TABLE-continued

No. Chemical formulae of the compounds according to the invention from Examples 1 to 12

B11

$(C_8F_{17}—C_{16}F_{33})—CH_2CH_2O—CONH$
$(C_8F_{17}—C_{16}F_{33})—CH_2CH_2O—(CH_2CHO)_2—CONH$
    |
    $CH_2Cl$ $A—NHCO—O—$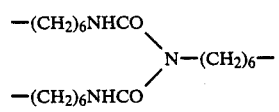$—OH$

B12

$\left[ (C_8F_{17}—C_{16}F_{33})—CH_2CH_2O—(CH_2CHO)_2—CONH \atop \qquad\qquad\qquad | \atop \qquad\qquad\qquad CH_2Cl \right]_2 —A—NHCO—O—$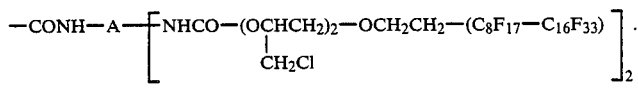$—COOH$ In the formulae B1 to B12,
A represents $-(CH_2)_6NHCO$
$\qquad\qquad\quad \diagdown$
$\qquad\qquad\quad\quad N—(CH_2)_6—$
$\qquad\qquad\quad \diagup$
$-(CH_2)_6NHCO$ (cf. abovementioned formula 10).

In the formulae B1 to B7, $B_1$ represents $—CONH—A—\left[ NHCO—(OCHCH_2)_2—OCH_2CH_2—(C_8F_{17}—C_{16}F_{33}) \atop \qquad\qquad\quad | \atop \qquad\qquad\quad CH_2Cl \right]_2 .$ In the formula B8, $B_2$ represents $\qquad\qquad NHCO—(OCHCH_2)_2—OCH_2CH_2—(C_8F_{17}—C_{16}F_{33})$
$\qquad\quad \diagup \qquad\qquad |$
$—CONH—Ai \qquad\qquad CH_2Cl$
$\qquad\quad \diagdown$
$\qquad\qquad NHCO—OCH_2CH_2—(C_8F_{17}—C_{16}F_{33})$

THE USE OF THE COMPOUNDS ACCORDING TO THE INVENTION

Examples I to XII

In Examples I to XII, the compounds B1 to B12 according to the invention were tested by means of a customary spinning dressing for polyamide fibers which contained in each case approx. 150 g of compound according to the invention per 1,000 g of spinning dressing (the spinning dressing was thus composed of water as the main component, the customary ethoxylated fatty alcohols and long-chain amine oxides as dressing agents and approx. 15% by weight of compound according to the invention). Each of the twelve spinning dressings was used to treat identical polyamide 6 filaments in order to apply sufficient of the compound according to the invention and of the dressing agent to the filaments for 0.05% by weight of fluorine and 1% by weight of dressing agent to be present on the filaments, percentages by weight relating in each case to weight of the filaments. This was effected by drawing the filaments through the spinning dressing in a customary manner, drying them and keeping them at a temperature of 200° C. for 30 seconds (heat treatment and condensation). A woven fabric was prepared from each of the filaments treated in this way. This gave 12 woven fabrics containing the compounds B1 to B12 according to the invention, a 0.05% by weight fluorine coating and a 1% by weight coating of dressing agent being present on each woven fabric, percentages by weight relating in each case to the weight of the woven fabric.

The oil repellency (oleophobic character) of the twelve woven fabrics was tested as specified in AATCC Testing Standard 1181966 and their water repellency (hydrophobic character) was tested as specified in DIN 53,888-1965, these tests being carried out after the condensation reaction described and after the condensed woven fabrics had been treated for 3 hours by alkaline washing at the boil. In this treatment, the individual woven fabrics were boiled in a customary manner for 3 hours in an alkaline wash liquor and were then dried; the composition of the wash liquor was 1 liter of water, 1 g of trisodium phosphate and 2 g of a fatty acid polyglycol ester obtained by oxethylating butane-1,4-diol with 15 moles of ethylene oxide and subsequently esterifying the oxethylate with 1 mole of oleic acid.

The results of Examples I to XII are summarized below:

| Examples and compounds tested | Oil repellency | | Water repellency | |
|---|---|---|---|---|
| | After the condensation reaction | After washing at the boil | After the condensation reaction | After washing at the boil |
| I/B1 | 6 | 3 | 5 | 4 |
| II/B2 | 6 | 3 | 5 | 4 |
| III/B3 | 6 | 4 | 5 | 4 |
| IV/B4 | 5 | 4 | 4 | 4 |
| V/B5 | 5 | 4 | 4 | 4 |
| VI/B6 | 5 | 4 | 5 | 4 |
| VII/B7 | 5 | 4 | 5 | 4 |
| VIII/B8 | 6 | 5 | 5 | 4 |
| IX/B9 | 5 | 5 | 5 | 4 |
| X/B10 | 5 | 4 | 4 | 3 |
| XI/B11 | 5 | 4 | 4 | 3 |
| XII/B12 | 5 | 4 | 5 | 4 |

The AATCC Test 118—1966 (American Association of Textile Chemists and Colorists) and DIN 53,888-1965 (Desutsche Industrie-Norm) are described below:

As is known, the oil repellency value is determined as specified in AATCC Test 118-1966 by putting three drops of a specific test liquid (see below) carefully on the textile material to be tested. Treatment time: 30 seconds. The value indicated is that at which no apparent wetting of the woven fabric under the drops has been caused (after the expiry of the treatment time):

| Test liquid | Oil repellency value |
|---|---|
| Paraffin oil | 1 |
| 65/35 Paraffin oil/n-hexadecane | 2 |
| n-hexadecane | 3 |
| n-tetradecane | 4 |
| n-dodecane | 5 |
| n-decane | 6 |
| n-octane | 7 |
| n-heptane | 8 |

An oil repellency value of 1 denotes the worst repellency effect and an oil repellency value of 8 denotes the best effect.

As is known, the water repellency value is determined as specified in DIN 53,888-1965 by exposing the textiles to be tested to rain under standardized conditions, the underside of the textile sample being subjected to mechanical rubbing at the same time. The water-repellent effect is assessed visually using the ratings 1 to 5, rating 1 denoting the poorest water-repellent effect and rating 5 the best effect.

The test results show that a very high oil-repellency and water-repellency is achieved by means of the urethanes according to the invention, and that the urethanes according to the invention can also be added to textile treatment dressings.

We claim:

1. A urethane formed from aliphatic fluoroalcohols, isocyanates and aromatic compounds and having the formula 1 below

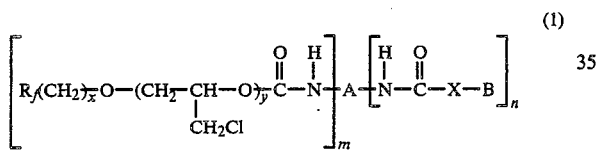  (1)

in which
R$_f$ denotes a perfluoroalkyl group having 4 to 20 carbon atoms, or an R'$_f$SO$_2$NR$_1$ group in which R'$_f$ is a perfluoroalkyl group having 4 to 20 carbon atoms, and R$_1$ is H or an alkyl group having 1 to 4 carbon atoms, x denotes an integer from 1 to 4, y denotes a number from 0 to 10, m denotes a number from 1 to 2 and n denotes a number from 1 to 2, the sum of m+n being not more than 3, A denotes one of the groups corresponding to the formulae 2 to 10 below

  (2)

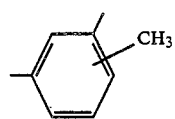  (3)

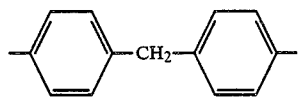  (4)

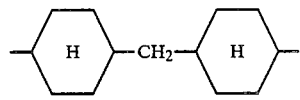  (5)

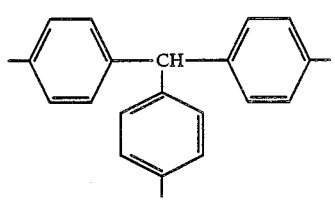  (6)

  (7)

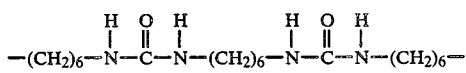  (8)

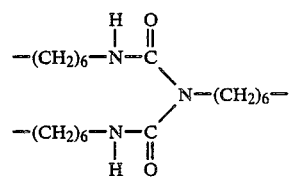  (9)

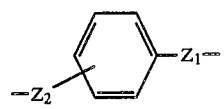  (10)

X denotes one of the groups corresponding to the formulae 11 to 19 below, which can be monosubstituted or polysubstituted by an alkyl group having 1 to 4 carbon atoms

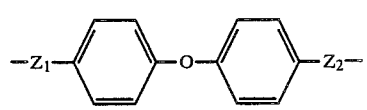  (11)

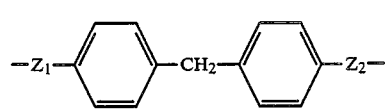  (12)

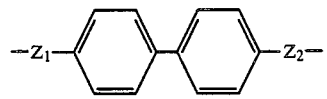  (13)

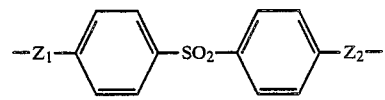  (14)

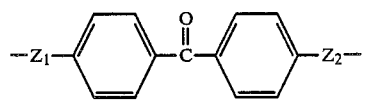  (15)

(16)

-continued

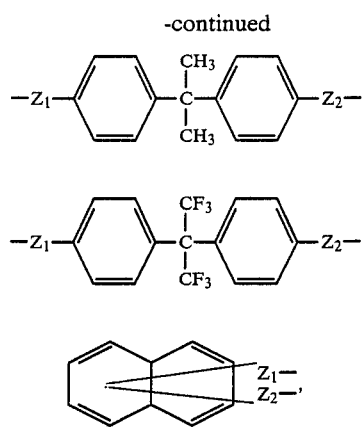

(17)

(18)

(19)

in which $Z_1$ and $Z_2$ represent O, NH or COO in which the two substituents are not identical; in the case where $Z_1$ and $Z_2$ are COO, the carbonyl of the COO group is attached to the aromatic ring; or $Z_1$ and $Z_2$ represent O or NH in which the two substituents are identical, and B denotes a hydrogen atom, an alkyl group having 1 to 4 carbon atoms or a group corresponding to the formula 20 below

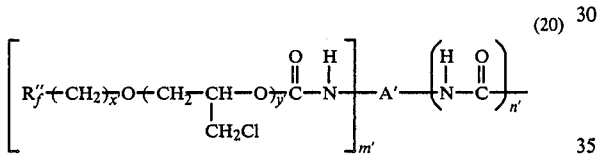

(20)

in which $R''_f$, $x'$, $y'$, $m'$, $n'$ and $A'$, have one of the meanings of $R_f$, $x$, $y$, $m$, $n$ and $A$, respectively.

2. A urethane as claimed in claim 1, in which:
$R_f$ denotes a perfluoroalkyl group having 6 to 16 carbon atoms,
x denotes 2,
y denotes 1 to 5,
m denotes 1 to 2,
n denotes 1 to 2, the sum of m+n being not more than 3,
A denotes a toluylene group or one of the three groups corresponding to the formulae 8 to 10,
X denotes a group corresponding to the formulae 11, 15, 16, 17 or 18 and
B denotes H or a group corresponding to the formula 20 in which $A'$ is one of the three groups corresponding to the formulae 8 to 10.

3. A urethane as claimed in claim 1, in which:
$R_f$ denotes a perfluoroalkyl group having 6 to 16 carbon atoms,
x denotes 2,
y denotes 1 to 5,
m denotes 1 to 2,
n denotes 1 to 2, the sum of m+n being not more than 3,
A denotes a toluylene group or one of the three groups corresponding to the formulae 8 to 10,
X denotes a group corresponding to the formulae 11, 15, 16, 17 or 18 and
B denotes H or a group corresponding to the formula 20 in which $A'$ is one of the three groups corresponding to the formulae 8 to 10, $R''_f$ is a perfluoroalkyl group having 6 to 16 carbon atoms, $x'$ is 2, $y'$ is 1 to 5, $m'$ is 1 to 2 and $n'$ is 1 to 2, the sum of $m'+n'$ being not more than 3.

* * * * *